(12) United States Patent
Sidransky

(10) Patent No.: US 7,252,935 B2
(45) Date of Patent: Aug. 7, 2007

(54) METHOD OF DETECTION OF PROSTATE CANCER

(75) Inventor: David Sidransky, Baltimore, MD (US)

(73) Assignee: The John Hopkins University School of Medicine, Baltimore, MD (US)

( * ) Notice: Subject to any disclaimer, the term of this patent is extended or adjusted under 35 U.S.C. 154(b) by 470 days.

(21) Appl. No.: 10/295,483

(22) Filed: Nov. 15, 2002

(65) Prior Publication Data

US 2003/0124600 A1 Jul. 3, 2003

Related U.S. Application Data

(60) Provisional application No. 60/333,296, filed on Nov. 16, 2001.

(51) Int. Cl.
*C12Q 1/70* (2006.01)
*C12P 19/34* (2006.01)

(52) U.S. Cl. .................... 435/6; 435/91.1; 435/91.2

(58) Field of Classification Search .............. None
See application file for complete search history.

(56) References Cited

OTHER PUBLICATIONS

AstraZeneca, Classification of prostate cancer (2003) ProstateLine.com, Prostate cancer, classification: pp. 1-5.*

Eads, et al., *MethyLight: a High-Throughout Assay to Measure DNA Methylation*, Nucleic Acids Research, 2000, vol. 27, No. 8, pp. e32, i-viii.
Brooks, et al., *CG Island Methylation Chagnes Near the GSTP1 Gene in Prostatic Intraepithelial Neoplasia*, Cancer Epidemiology, Biomarkers & Prevention, Jun. 1998, vol. 7, pp. 531-536.
Goessl, et al., *DNA-Based Detection of Prostate Cancer in Blood, Urine, and Ejaculates*, Annals New York Academy of Sciences, Sep. 1, 2001, vol. 945, No. 1, pp. 51-58.
Goessl, et al., *DNA-Based Detection of Prostate Cancer in Washings From Tansrectal Biopsies*, Virchows Archives, 2000, vol. 439, P-400, p. 398.
Ahern, Holly, *Biochemical, Reagent Kits Offer Scientists Good Return on Investment*, The Scientist, Jul. 24, 1995, vol. 9, No. 15, pp. 1-5.
Goessl, et al., *Fluorescent Methylation-Specific Polymerase Chain Reaction for DNA-Based Detection of Prostate Cancer in Bodily Fluids*, Cancer Research, Nov. 1, 2001, vol. 60, pp. 5941-5945.
Chu, et al., *The Use of Real-Time Quantitative Polymerase Chain Reaction toDetect Hypermethylation of the CPG Islands in the Promoter Region Flanking the GSTP1 Gene to Diagnose Prostate Carcinoma*, The Journal of Urology, Apr. 2002, vol. 167, pp. 1854-1858.

* cited by examiner

*Primary Examiner*—Jeffrey Fredman
*Assistant Examiner*—David C. Thomas
(74) *Attorney, Agent, or Firm*—DLA Piper US LLP

(57) ABSTRACT

The present invention provides methods and kits useful for detecting neoplasia by measuring the methylation level of biomarkers, especially the promoter region of GSTP1 for the detection of prostate adenocarcinoma.

32 Claims, 3 Drawing Sheets

METHOD OF DETECTION OF PROSTATE CANCER

RELATED APPLICATION DATA

This application claims priority under 35 U.S.C. 119(e) to U.S. Provisional Patent Application Ser. No. 60/333,296, filed Nov. 16, 2001, which is incorporated by reference in its entirety.

STATEMENT OF GOVERNMENT SUPPORT

This invention was made in part with government support under NIH Grant No. 1U01CA84986 awarded by the National Institutes of Health (NIH). The government may have certain rights in this invention.

FIELD OF THE INVENTION

This invention relates generally to the field of methylation status of genes and regulatory elements and more specifically to detection of prostate cancer by conventional and quantitative PCR methods.

BACKGROUND OF THE INVENTION

Prostatic adenocarcinoma is the most commonly diagnosed non-cutaneous cancer for men in the United States. The incidence is likely to continue to increase as people survive longer and more middle-aged men undergo routine screening for the disease. Men diagnosed with early stage small volume disease have the best outcome following curative treatment. Therefore the aim of early detection programs is to diagnose cancer at an early curable stage.

The gold standard algorithm for diagnosis currently entails digital rectal exam and measurement of serum prostate-specific antigen (PSA) and if either is suspicious it is followed by trans-rectal prostatic needle biopsy. However, serum PSA can be elevated in benign conditions and needle biopsy may fail to identify even significant amounts of cancer due to sampling error. Therefore, the introduction of additional diagnostic tests is needed to improve the sensitivity of prostate cancer diagnosis.

Although several specific genetic alterations have been described in prostate adenocarcinoma, such as TP53 and PTEN inactivation, the single most common and earlier of these is methylation of the 5'-regulatory region of the GSTP1 gene. The detection of this epigenetic alteration in bodily fluids has been successfully accomplished using DNA-based techniques. However, these earlier studies either included only a relatively small number of patients or focused mainly on cases of advanced disease.

Recently, a specific real-time quantitative methyl specific PCR (RTQ-MSP) method, allowing the performance of non-isotopic, rapid, and highly accurate quantitative amplification analysis via the continuous optical monitoring of a fluorogenic PCR assay was developed. The application of this method to evaluate the methylation status of the p16 gene in bone marrow aspirates from patients with multiple myeloma, revealed complete concordance with conventional MSP (C-MSP) analysis. In this same study, it was shown that RTQ-MSP was sensitive enough to detect down to 10 genome equivalents of methylated p16 sequence.

However, there is a need in the art to develop sensitive and accurate early stage diagnostic assays for detecting prostate adenocarcinoma.

SUMMARY OF THE INVENTION

The present invention is based, in part, on the discovery that quantitative measurement of the methylation level of biomarkers, e.g., promoter region of glutathione-S-transferase (GSTP1), can be used to detect neoplasia. Accordingly, the present invention provides methods and kits useful for detecting neoplasia, especially prostate adenocarcinoma. In one embodiment, the present invention provides a method for detecting prostate neoplasia. The method includes determining a methylation ratio of a sample, e.g., a tissue sample from a subject. The methylation ratio is a ratio between the level of methylation of a promoter region, e.g., of glutathione-S-transferase (GSTP1), relative to the level of methylation of a region of a reference gene. If the methylation ratio is higher in the sample, e.g., tissue, from the test subject than the methylation ratio in a sample, or tissue from normal subjects or from a tissue or sample from a subject with hyperplasia, it is indicative of prostate neoplasia in the test subject.

In another embodiment, the present invention provides a method for detecting prostate neoplasia by determining the methylation level of a promoter region of glutathione-S-transferase (GSTP1) in a sample of bodily fluid, such as urine or serum, from a subject. The methylation level is determined using a conventional polymerase chain reaction (PCR), or the real-time/quantitative PCR method. If the methylation level is higher in the test subject than the methylation level in a normal subject it is indicative of prostate neoplasia in the subject.

In yet another embodiment, the present invention provides a kit for detecting prostate hyperplasia. The kit includes a first container containing a pair of primers for amplification of a promoter region of glutathione-S-transferase (GSTP1), a second container containing a pair of primers for amplification of a region of a reference gene, and a third container containing a first and second oligonucleotide probe, with the first oligonucleotide probe specific for the amplification of the promoter region of GSTP1 and the second oligonucleotide probe specific for the amplification of the region in the reference gene. In one aspect, at least one of the primers for the amplification of the promoter region of GSTP1 or one of the oligonucleotide probes is capable of distinguishing between methylated and unmethylated nucleic acid.

In another aspect, the kit contains a first container containing a pair of primers for amplification of a promoter region of glutathione-S-transferase (GSTP1), with the primers being capable of distinguishing between methylated and unmethylated nucleic acid, and an instruction disclosing that the kit is useful for detecting prostate adenocarcinoma in a bodily fluid sample from a subject and that a methylation level of the promoter region of GSTP1 as determined by conventional polymerase chain reaction using the primers in the first container that is higher than the methylation level of the promoter region of GSTP1 in a normal subject is indicative of prostate adenocarcinoma in the subject with a sensitivity no less than 40%.

In another embodiment, the present invention provides a method for detecting prostate neoplasia by amplifying a promoter region of glutathione-S-transferase (GSTP1) in a biological sample from a subject by means of oligonucleotide primers in the presence of at least one specific oligonucleotide probes, with the promoter region being modified by an agent that modifies unmethylated cytosine to produce a converted nucleic acid and at least one oligonucleotide primer or specific oligonucleotide probe being capable of distinguishing between unmethylated and methylated nucleic acid, and determining the methylation level of the promoter region by determining the amplification level of the promoter region based on amplification-mediated displacement of the specific oligonucleotide probe. If the methylation level is higher in the test subject than the methylation level in a normal subject, it is indicative of prostate neoplasia in the subject.

DETAILED DESCRIPTION OF THE INVENTION

Figure 1:
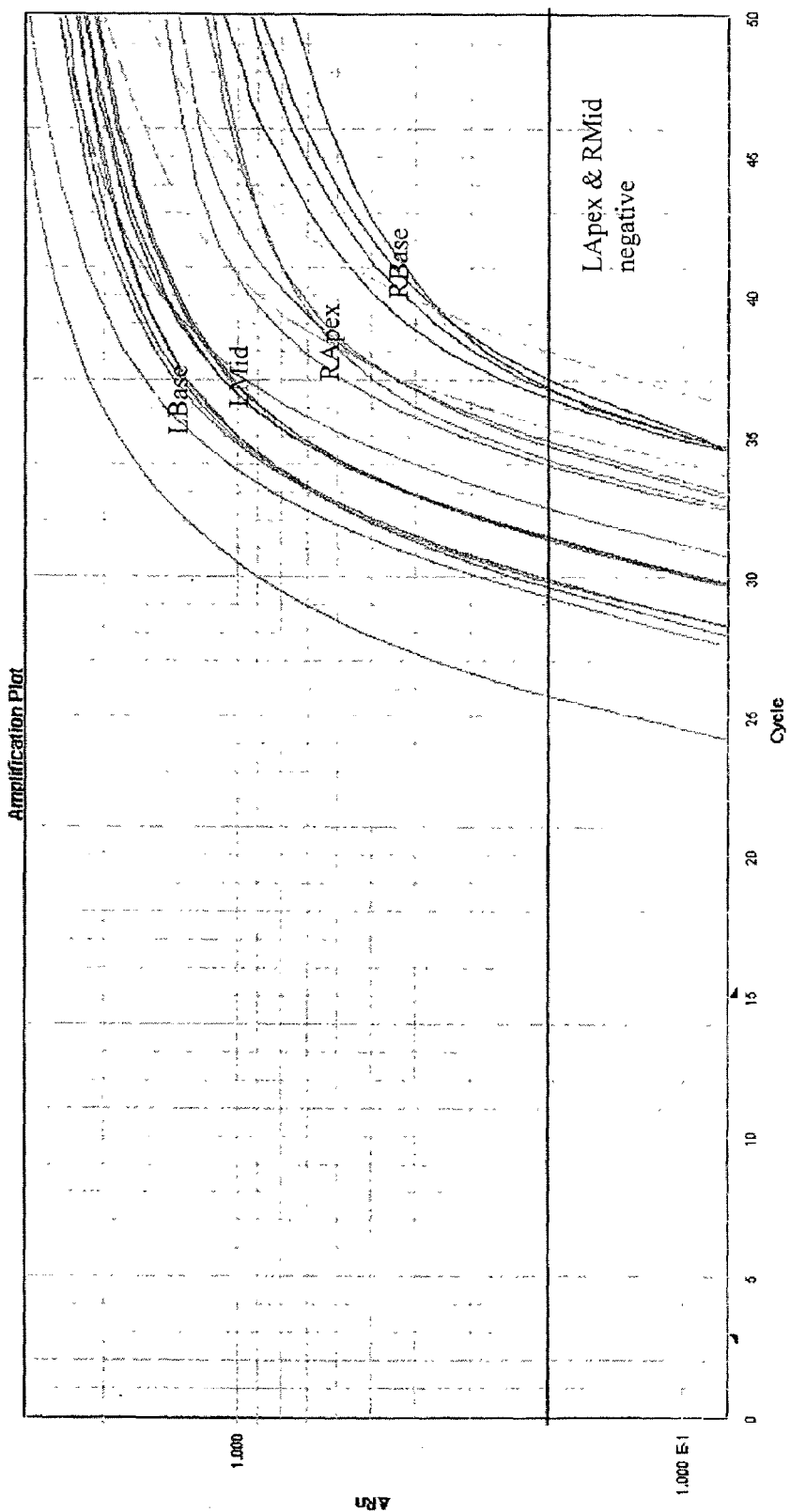
FIG. 1 shows the amplification curves for a case positive for carcinoma by GSTP1 QMSP on 4/6 biopsies (LB=left base, LM=left mid, RA=right apex, RB=right base). Each biopsy was run in quadruple and compared to standard dilutions of positive control (S1-5=100 ng, 10 ng, 1 ng, 100 pg, 10 pg standard DNA respectively). This case was also positive for carcinoma by histology on 2/6 biopsies (Left Base 2 mm, Left Mid 1 mm). The extent of tumor seen histologically on biopsy corresponded to the levels of GSTP1 methylation measured.

The present invention is based, in part, on the discovery that quantitative measurement of methylation level of biomarkers, e.g., promoter region of glutathione-S-transferase (GSTP1), can be used to detect neoplasia, e.g., prostate adenocarcinoma. Accordingly, the present invention provides methods and kits useful for detecting neoplasia, especially prostate adenocarcinoma by determining the methylation level or ratio of biomarkers.

According to one aspect of the present invention, neoplasia in a cell or tissue can be detected by quantitatively measuring the methylation level of one or more biomarkers. The biomarkers of the present invention can be any marker whose methylation level is characteristically associated with the abnormal growth or proliferation of a cell or tissue. For example, the methylation levels of various tumor suppressor genes are associated with neoplasia or tumor growth and can be used as biomarkers of the present invention. In one embodiment, the biomarker of the present invention is glutathione-S-transferase (GSTP1).

In another embodiment, the biomarker is a promoter region of GSTP1. The promoter region of GSTP1 can be any region within the promoter of GSTP1, e.g., any region containing one or more sites associated with methylation such as CpG dinucleotides and suitable for quantitative measurement such as amplification by polymerase chain reaction (PCR). The promoter of GSTP1 usually includes the regulatory region located upstream or 5' to GSTP1.

Sequence analysis of the promoter region of GSTP1 shows that nearly 72% of the nucleotides are CG and about 10% are CpG dinucleotides.

According to the present invention, neoplasia in a cell or tissue can be detected by quantitatively measuring the methylation level of one or more biomarkers using, e.g., real-time polymerase chain reaction (PCR) with at least one oligonucleotide primer or oligonucleotide specific probe being capable of distinguishing between methylated and unmethylated nucleic acid. In general, a quantitatively measured methylation level in a biological sample from a subject, e.g., human that is higher than the quantitatively measured methylation level in a biological sample from a normal subject is indicative of neoplasia in the subject.

A normal subject as used in the present invention can be any subject that does not have detectable neoplasia by means other than the methods provided by the present invention. For example, a normal subject for prostate adenocarcinoma can be any human that does not have any clinical symptom of prostate adenocarcinoma, a normal PSA level, and a histological diagnosis free of prostate adenocarcinoma. In general, a level associated with a normal subject as used in the present invention includes statistically obtained value associated with a population of normal subjects. For example, the methylation level in a normal subject as used in the present invention includes the mean or average methylation level and a range for a statistically significant population of normal subjects.

The biological sample of the present invention can be any sample suitable for the methods provided by the present invention. In one embodiment, the biological sample of the present invention is a tissue sample, e.g., a biopsy specimen such as samples from needle biopsy. In another embodiment, the biological sample of the present invention is a sample of bodily fluid, e.g., serum, plasma, urine, and ejaculate.

According to one embodiment of the present invention, prostate adenocarcinoma in a cell or tissue can be detected by quantitatively measuring the methylation level of the promoter region of GSTP1, e.g., using real-time methylation specific PCR. For example, the methylation level of the promoter region of GSTP1 can be determined by determining the amplification level of the promoter region of GSTP1 based on amplification-mediated displacement of one or more probes whose binding sites are located within the amplicon.

In general, real-time quantitative methylation specific PCR is based on the continuous monitoring of a progressive fluorogenic PCR by an optical system. Such PCR systems usually use two amplification primers and an additional amplicon-specific, fluorogenic hybridization probe that specifically binds to a site within the amplicon. The probe can include one or more fluorescence label moieties. For example, the probe can be labeled with two fluorescent dyes: 1) a 6-carboxy-fluorescein (FAM), located at the 5'-end, which serves as reporter, and 2) a 6-carboxy-tetramethyl-rhodamine (TAMRA), located at the 3'-end, which serves as a quencher. When amplification occurs, the 5'-3' exonuclease activity of the Taq DNA polymerase cleaves the reporter from the probe during the extension phase, thus releasing it from the quencher. The resulting increase in fluorescence emission of the reporter dye is monitored during the PCR process and represents the number of DNA fragments generated.

In one embodiment, oligonucleotide primers are designed to specifically bind methylated primer binding sites, e.g., bisulfite-converted DNA within the 3'-end of the promoter region of the GSTP1 gene, and a probe is designed to anneal specifically within the amplicon during extension. In another embodiment, oligonucleotide primers are designed to bind either methylated or unmethylated primer binding sites and the probe is designed to anneal specifically to methylated probe binding site, e.g., bisulfite-converted binding site. In yet another embodiment, oligonucleotide primers and probes are designed to specifically bind methylated binding sites, e.g., bisulfite-converted binding sites.

According to another aspect of the present invention, neoplasia of a biological sample is indicated when a methylation ratio of a biomarker is higher than the methylation ratio in a normal subject. The methylation ratio of the present invention includes the ratio of the methylation level of a biomarker and the level of a region in a reference gene determined by the same means used for the determination of the methylation level of the biomarker. Usually, the methylation ratio of the present invention is represented by the ratio of the methylation level of a biomarker and the level of a region in a reference gene determined by the same means used for the determination of the methylation level of the biomarker.

In one embodiment, the methylation ratio of the present invention is the ratio of the methylation level of a biomarker and the level of a region of a reference gene, both of which are quantitatively measured using real-time polymerase chain reaction (PCR). For example, the methylation level of a biomarker from a sample of a subject can be quantitatively measured using a pair of primers and an oligonucleotide probe, where one primer, both primers, the oligonucleotide probe, or both primers and the oligonucleotide probe are capable of distinguishing between methylated and unmethylated nucleic acid, e.g., after the nucleic acid being modified by a modifying agent, e.g., bisulfite converting unmethylated cytosine to a converted nucleic acid.

In another embodiment, the methylation ratio of the present invention is the ratio of the methylation level of a promoter region of GSTP1 and the level of a region of a reference gene, both of which are quantitatively measured using real-time PCR. In yet another embodiment, the methylation ratio of the present invention is the ratio of the methylation level of a promoter region of GSTP1 measured by methylation specific real-time PCR and the level of a region of a reference gene measured by real-time PCR.

The region of a reference gene of the present invention can be any region of a gene having one or more sites or regions that are devoid of methylation sites, e.g., devoid of CpG dinucleotides. For example, the region of a reference gene can be a region that having two primer binding sites for amplification such as PCR that are devoid of CpG dinucleotides or a region having at least one specific oligonucleotide probe binding site for real-time PCR that is devoid of CpG dinucleotides. In one aspect, the region of a reference gene of the present invention is a region of MYOD gene. In another aspect, the region of a reference gene of the present invention is a region of ACTB gene. In yet another embodiment, the region of a reference gene of the present invention is a region that is not frequently subject to copy number alterations, such as gene amplification or deletion.

In general, according to the present invention the level of a region of a reference gene is quantitatively measured using real-time PCR with primers and specific probes that specifically bind to sites after bisulfite conversion but without discriminating directly or indirectly the methylation status of the sites.

According to one embodiment of the present invention, prostate adenocarcinoma is indicated in a subject when a methylation ratio of a promoter region of GSTP1 in a biological sample from the subject is greater than 5, or 10, as the methylation ratio is represented by the ratio of the methylation level of a promoter region of GSTP1 and the level of a region of a reference gene, e.g., MYOD or ACTB times 1000 fold. For example, when a methylation ratio times 1000 is greater than 3, or 5 or even 10, it is indicative of prostate adenocarcinoma in the subject.

According to another aspect of the present invention, the methylation ratio of the present invention can be used for diagnosing neoplasia either independently or in combination with other diagnostic methods, e.g., diagnostic methods based on genomic information, proteomic assessment, or histological analysis of tissue samples. In one embodiment, the methylation ratio of the present invention is used independently or in combination with histological analysis in detecting neoplasia.

In another embodiment, the methylation ratio of a promoter region of GSTP1 is used independently of histological analysis for the detection of prostate adenocarcinoma. In general, according to the present invention the methods of using methylation ratio for detection of prostate adenocarcinoma as provided by the present invention is more sensitive than the histological analysis in its currently available form. A subject having a methylation ratio of a promoter region of GSTP1 higher than the methylation ratio in a normal subject, e.g., greater than 5 or 10, is indicative of prostate adenocarcinoma in light of the fact that the subject is determined free of prostate adenocarcinoma by histological analysis.

Alternatively, the methylation ratio of a promoter region of GSTP1 can be used in combination with histological analysis for the detection of prostate adenocarcinoma. For example, according to the present invention detection of prostate adenocarcinoma in a subject can include determination of the methylation ratio and a histological analysis of prostate tissue samples, e.g., needle biopsy from the subject and a higher than normal methylation ratio, e.g., greater than 5 or 10, either alone or in combination with a histological diagnosis of prostate adenocarcinoma is indicative of prostate adenocarcinoma.

In yet another embodiment, the methylation ratio of the present invention can be used independently or in combination with diagnostics based on proteomic assessment. For example, according to the present invention the methylation ratio of a promoter region of GSTP1 in a subject can be used either independently or in association with the determination of PSA level in the subject in detecting prostate adenocarcinoma.

According to the present invention, the methylation ratio of a promoter region of GSTP1 generally does not directly correlate with the PSA level, thus the methylation ratio can be used as an assessment independent of the PSA level for detecting prostate adenocarcinoma, e.g. a higher than normal methylation ratio of a promoter region of GSTP1 in a subject is indicative of prostate adenocarcinoma in the subject with a normal PSA level. Likewise, the methylation ratio can rule out cancer in a subject with a falsely high PSA value. Alternatively, detection of prostate adenocarcinoma can include determining the methylation ratio of a promoter region of GSTP1 and the PSA level; a higher than normal methylation ratio either alone or in association with an abnormal PSA level is indicative of prostate adenocarcinoma.

According to another aspect of the present invention, different ways for determination of the methylation level of biomarkers in association with different types of biological samples from a subject provide different levels of sensitivity with respect to neoplasia detection. For example, according to the present invention for bodily fluid samples determination of the methylation level of biomarkers using conventional PCR generally provides better sensitivity than the sensitivity obtained by using real-time PCR.

In one embodiment, the methylation level of a promoter region of GSTP1 in a bodily fluid sample, e.g., not limited to serum, plasma, urine, or ejaculate as determined by conventional or non-real-time PCR provides better sensitivity for prostate adenocarcinoma detection than the sensitivity obtained by using real-time PCR. Therefore, according to the present invention the methylation level of a promoter region of GSTP1 in a sample from bodily fluid from a subject can be determined by using conventional non-real-time PCR, or real-time PCR and a methylation level higher than the methylation level in a normal subject is indicative of prostate adenocarcinoma, e.g., in light of the fact that the subject has a normal methylation level of the promoter region of GSTP1 as determined by real-time PCR.

According to another aspect of the present invention, it provides kits useful for detecting neoplasia in a cell or tissue, e.g., using the methods provided by the present invention for the detection of neoplasia. In one embodiment, the present invention provides a kit, e.g., a compartmentalized carrier including a first container containing a pair of primers for amplification of a biomarker, a second container containing a pair of primers for amplification of a region in a reference gene, and a third container containing a first and second oligonucleotide probe specific for the amplification of the biomarker and the region of the reference gene, respectively.

In another embodiment, the kit provided by the present invention further includes a fourth container containing a modifying agent that modifies unmethylated cytosine to produce a converted nucleic acid, e.g., uracil. Any suitable modifying agent can be included in the kit provided by the present invention. For example, the modifying agent can be sodium bisulfite.

In yet another embodiment, the kit provided by the present invention further includes a probe for PSA determination. In still another embodiment, the kit provided by the present invention further includes an instruction insert disclosing normal and/or abnormal methylation ratio ranges for the detection of neoplasia, describing the types of samples suitable or unsuitable for the application of the kit, and/or the specificity or sensitivity provided by the assays utilizing the kit of the present invention.

According to one embodiment of the present invention, the kit provided by the present invention includes a first container containing at least one pair of primers for amplification of a promoter region of GSTP1, a second container containing at least one pair of primers for amplification of a region of a reference gene, and a third container containing a first and second oligonucleotide probe specific to the amplification of the promoter region of GSTP1 and the region of the reference gene, respectively, provided that one or both primers for amplification of the promoter region of GSTP1 or one or more first oligonucleotide probes specific to the amplicon of the promoter region of GSTP1 are capable of distinguishing between methylated and unmethylated nucleic acid, either directly or indirectly, e.g., after bisulfite modification. Optionally the kit provided by this embodiment of the present invention can further include an instruction insert, e.g., disclosing that a methylation ratio times 1000 of a promoter region of GSTP1 of the present invention that is greater than 3, 5, or 10, is indicative of prostate adenocarcinoma or that the kit can be used with a prostate tissue sample, e.g., most suitable to be used with a prostate tissue sample.

The present invention also provides a kit useful for detecting prostate adenocarcinoma, especially in bodily fluid samples. The kit includes a first container containing at least one pair of primers capable of distinguishing between methylated and unmethylated nucleic acid for amplification of a promoter region of GSTP1 and an instruction insert disclosing, among other things, that the kit is useful for detecting prostate adenocarcinoma in a bodily fluid sample of a subject and that a methylation level of the promoter region of GSTP1 as determined by conventional or non-real-time PCR using the primers provided that is higher than the methylation level of the promoter region of GSTP1 in a normal subject is indicative of prostate adenocarcinoma in the subject with a sensitivity no less than 40%.

EXAMPLES

The following examples are intended to illustrate but not to limit the invention in any manner, shape, or form, either explicitly or implicitly. While they are typical of those that might be used, other procedures, methodologies, or techniques known to those skilled in the art may alternatively be used.

Example 1

Quantitative GSTP1 Methylation Improves the Detection of Prostate Adenocarcinoma Sextant Biopsies In this study, a direct comparison of GSTP1 QMSP was done with standard histological review of needle biopsies to see if it could improve the sensitivity of cancer diagnosis. Analysis of sextant biopsies allowed direct comparison of the two approaches on tissue with subsequent final pathological diagnosis. The combination of histology with GSTP1 could significantly improve the diagnosis of prostate cancer without affecting specificity.

Materials and Methods

Patients and Sample Collection 56 patients undergoing prostatectomy for prostate adenocarcinoma (PSA range 0.5-25.8, median 5.0) and 16 patients undergoing cystoprostatectomy for bladder carcinoma at The Johns Hopkins Hospital between November 2001 and May 2002 were included in this study. Immediately after resection, sextant biopsies (from left and right apex, mid and base) were taken from all 72 resected prostate specimens using a thin (18 gauge) needle and promptly frozen at $-80°$ C.

All the needle biopsies were cut into 10 μm sections and placed in a mixture of 1% sodium dodecyl sulfate and proteinase K (0.5 mg/ml) at 48° C. overnight to digest. DNA was then extracted using phenol/chloroform and ethanol precipitation as previously described (10). In addition, 5 μm frozen sections were taken every 10 slices and stained with hematoxylin-eosin for blinded examination by light. All the resected prostates were then serially sectioned and totally submitted for histological examination, which was considered the gold standard for determining the presence of prostatic carcinoma.

Bisulfite Treatment

Sodium bisulfite conversion of 2 µg DNA from each biopsy sample was performed as described previously. Briefly, DNA samples were denatured with sodium hydroxide, incubated for 2 hours at 70° C. with sodium bisulfite and hydroquinone, purified using the Wizard purification kit (Promega, Madison, Wis.), further denatured and deaminated and finally ethanol precipitated. Samples were resuspended in 60 µl 10 mM Tris (pH 8).

Real-Time Quantitative MSP

The modified DNA samples were analyzed for methylation of GSTP1 using fluorogenic real-time QMSP. In addition samples were analyzed for amplification of 2 internal reference genes, ACTB and MYOD. Primers and probes for GSTP1(8), MYOD (8) and ACTB (9) have been described previously. Primers were obtained from Invitrogen (Gaithersburg, Md.) and probes from Applied Biosystems (Foster City, Calif.). Reactions were performed on 384 well plates using an Applied Biosystems 7900 Sequence Detector (Foster City, Calif.). The final (20 µl) reaction mix consisted of 600 nM each primer, 200 nM probe, 200 µM of each dATP, dCTP, dGTP, dTTP, 16.6 mM ammonium sulfate, 67 mM Trizma, 6.7 mM magnesium chloride, 10 mM mercaptoethanol, 0.1% dimethylsulfoxide and 3 µl (100 ng) modified DNA. Amplification conditions were 95° C. initiation for 2 mins, followed by 50 cycles at 95° C. for 15 secs and 60° C. for 1 min.

All samples were run in quadruple and were considered positive for GSTP1 if ¾ of the replicates showed amplification. Each PCR plate also included serial dilutions of 2 positive controls for construction of standard curves, a negative control and multiple water blanks. Leucocyte DNA from a healthy individual was used as the negative control. The same leucocyte DNA was methylated in vitro with excess Sss I Methyltransferase (New England Biolabs, Beverly, Mass.) to generate fully methylated DNA and used as one positive control. In addition, DNA from a human prostate cancer cell line, LNCaP (ATCC, Manassas, Va.), known to be methylated at the GSTP1 locus, was also run as a second positive control.

With this assay, detection of methylated GSTP1 DNA down to 4 genome equivalents was possible, determined by serial dilutions of the positive controls using a conversion factor of 6.6 pg DNA per diploid cell. The relative level of methylated GSTP1 in a particular sample was calculated using the ratio of the averaged GSTP1 value to the corresponding internal reference gene value. This ratio was then multiplied by 1000 for easier tabulation.

In this study we used 2 different reference genes, MYOD and ACTB. This was because we have converted from using MYOD as a reference gene to a more robust ACTB primer/probe set and wished to directly compare the previously reported GSTP1/MYOD (G/M) values to GSTP1/ACTB (G/A) values. All statistics and figures are based on the G/M values but G/A values were virtually identical and the same threshold values apply using this alternative reference gene.

Statistical Analysis

Exact binomial 95% confidence intervals are reported for all proportions. All analyses were done using the case as the unit of analysis. The statistical significance and precision of increases in sensitivity were calculated using a McNemar test, taking into account the pairing of readings within cases. The various sensitivity-specificity combinations produced by using different thresholds for GSTP1 are displayed in the form of receiver operator characteristic (ROC) curves. All calculations were performed with the statistical package Stata 7.0 (Stata Corp., College Station, Tex.).

Results

Seventy-two sets of biopsies, using both histology and GSTP1 methylation (56 known positives and 16 presumed negative) were analyzed in a blinded manner for the presence of prostate adenocarcinoma in the resection specimen. Final surgical pathology review of the cystoprostatectomy specimens detected clinically undiagnosed prostate adenocarcinoma in 5/16 (31%) cases, which increased the number of true positives to 61, leaving 11 true negative cases. This was taken to be the gold standard to which the blinded biopsy analysis by histology and GSTP1 methylation were compared. The pathological stages and grades of the 61 cases were: 19 T2a (Gleason 4-7), 29 T2b (Gleason 6-7), 11T3a (Gleason 6-7) and 2 T3b (one Gleason 7 and one ductal carcinoma).

Only 1 biopsy out of the 6 from each case needed to be called positive using either test for the case to be called positive by that test. Based on this, the sensitivity and specificity of histology and GSTP1 methylation as diagnostic tests were calculated separately and in combination (Table 1).

TABLE 1

Sensitivity and specificity for histology and GSTP1 QMSP using different thresholds

| Test | Sensitivity Histology and combined with GSTP1 | Sensitivity GSTP1 alone | Sensitivity increment for combined tests (95% CI) |
|---|---|---|---|
| Histology | 64% (39/61) | | |
| GSTP1 > 10 | 75% (46/61) | 70% (43/61) | 11% (5–22) |
| GSTP1 > 5 | 79% (48/61) | 75% (46/61) | 15% (7–26) |
| GSTP1 > 2 | 85% (52/61) | 82% (50/61) | 21% (12–34) |
| GSTP1 > 1 | 89% (54/61) | 89% (54/61) | 25% (15–37) |

Blinded histological assessment of the biopsies detected prostate adenocarcinoma in 39/61 cases, a sensitivity of 64% (CI 51-76%). The extent of carcinoma detected on biopsies for each case ranged from 0-20 mm, median 1 mm. All 11 true negative cases were found to be negative, a specificity of 100%. As the histologic criteria applied to the biopsy specimens was the same as that used for the total prostate examination, a specificity of 100% for biopsy would be expected unless the biopsy removed all abnormal cells, so the precision for this 100% estimate is higher than a statistical confidence interval would indicate, which assumes independence of a test and gold standard test.

Figure 2:
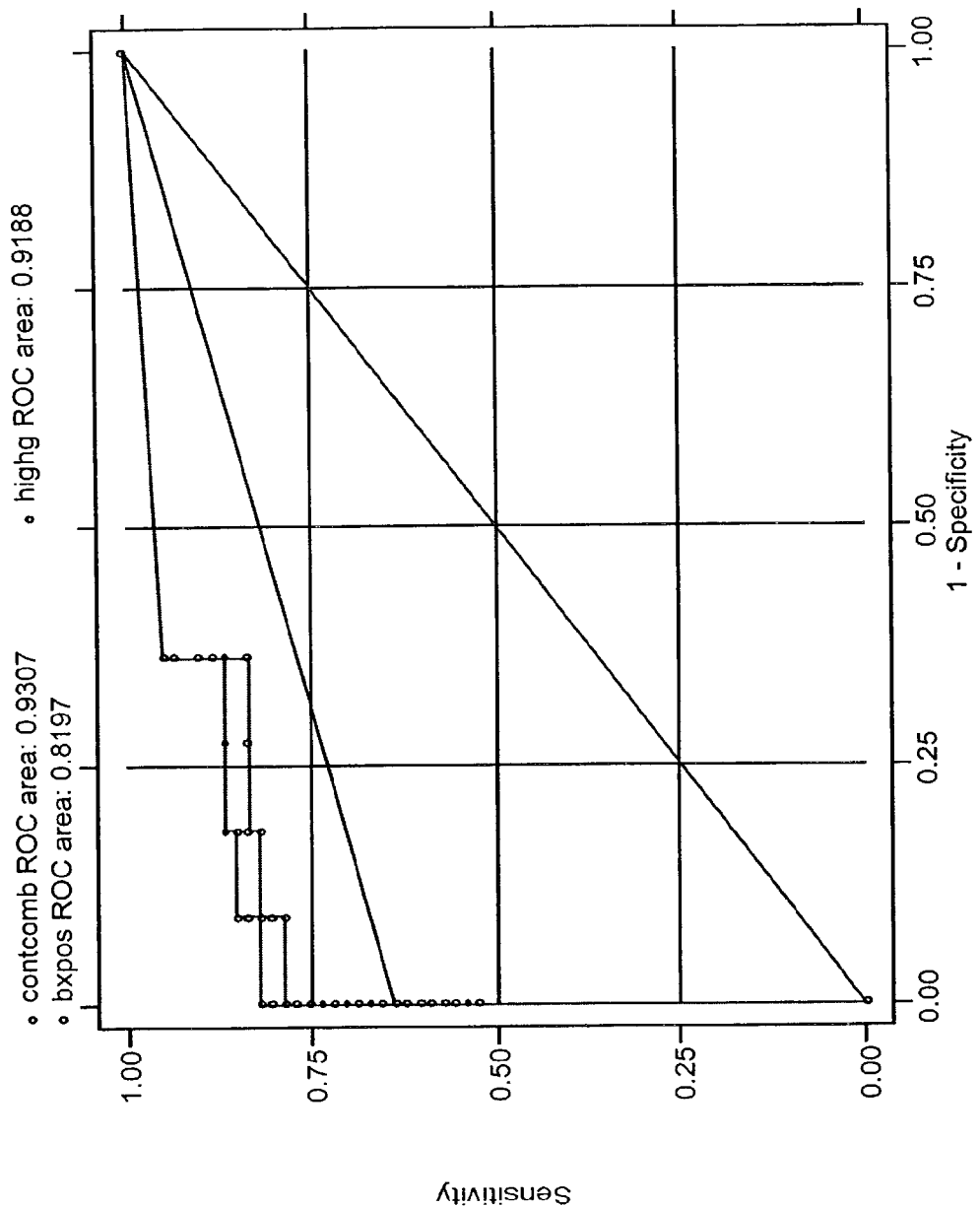
FIG. 2 shows the ROC curves for histology (blue), GSTP1 QMSP (green) and combined tests (red).

For GSTP1 alone, using the previously established threshold value of 10 in pilot studies, cancer was detected in 43/61 cases (range 0-791.4, median 41.3), a sensitivity of 70% (an example is shown in FIG. 1). All 11 true negative cases were found to be negative (range 0-2.5, median 0), a specificity of 100% (CI: 72%-100%). Using GSTP1 in combination with histology (defining positivity in either as a positive test), 46/61 cases were correctly diagnosed as positive, increasing sensitivity to 75%, an 11% (CI 5-22%) improvement over histology alone. A specificity of 100% was still maintained using a lower GSTP1 threshold of 5. For this threshold, GSTP1 alone had a sensitivity of 75% (46/61) {p=0.06 for being more sensitive than histology}. In combination with histology, 48/61 cases were correctly diagnosed, a sensitivity of 79% and a 15% (CI 7-26%) improvement over histology alone. ROC curves were used to display and contrast the performance of biopsy alone, GSTP1 alone and GSTP1 in combination with histology (FIG. 2)).

At the optimum threshold, GSTP1 QMSP analysis correctly diagnosed 9 cases of prostate cancer missed by histology and histology detected 2 cases missed by GSTP1 QMSP, which shows the importance of using both criteria. Pure primary tumor DNA samples from the 2 cases missed by QMSP were subsequently obtained by microdissection of paraffin block sections and analyzed for GSTP1 methylation (data not shown). One tumor was GSTP1 negative (0.1 mm carcinoma detected in one biopsy by histology); the other tumor was weakly GSTP1 positive and histology detected 1 mm and 0.1 mm carcinoma on 2/6 biopsies, yet GSTP1 values did not reach the positive threshold. For the 9 cases detected by GSTP1 QMSP but not histology, GSTP1 values ranged from 6.2 to 64.2 (median 13.0) and were positive in 2 biopsies for 3/9 and 1 biopsy for 6/9 cases. One case was an a typical extensive ductal carcinoma, 3 were small T2a and 5 were moderate to extensive T2a-b on formal surgical pathology review.

The 5 cystoprostatectomy cases found to incidentally contain prostate cancer included 2/5 containing a moderate extent of cancer (Gleason 7) present in both lobes, both of which were detected by GSTP1 QMSP and one of which was detected by histology on biopsy analysis; the remaining 3/5 cases each contained only a minute focus of carcinoma (Gleason grade 6 or lower) and were not detected by either test. The natural progression of these minute incidental lesions and appropriate therapy (if any) remains to be fully investigated.

In order to investigate whether GSTP1 could improve the sensitivity of routine diagnosis of prostate adenocarcinoma on needle biopsy, sextant biopsies taken from patients undergoing prostatectomy for previously diagnosed prostate adenocarcinoma and from patients undergoing cystoprostatectomy for bladder carcinoma, with no known diagnosis of prostate cancer were analyzed. These sextant biopsies were analyzed in a blinded manner for prostate adenocarcinoma in the resection specimen by histology and by GSTP1 QMSP.

At an optimal threshold of 5, the addition of GSTP1 QMSP analysis improved the sensitivity of diagnosis by 15% (from 64 to 79%) while maintaining 100% specificity. The marked improvement in the diagnosis of a cancer by the addition of a simple molecular test offers strong support for the use of GSTP1 methylation analysis prospectively as an adjunct to histology on diagnostic trans-rectal needle biopsies.

Histopathology is considered the gold standard by which the diagnosis of prostate cancer is established. However, on biopsies, sampling error and various technical artifacts are recognized as limitations of the approach. This study shows that a significant number of small cancers (22/61, 36%) can be missed by frozen section histological analysis of sextant biopsies. This included 18 out of 56 cases that had already been pre-selected with a previous histological diagnosis of prostate cancer based on a directed or random needle biopsy prior to prostatectomy. In a population of men undergoing diagnostic sextant biopsies, this number is likely to be similar or even higher.

Histology review on frozen sections is technically more difficult than from paraffin sections and this may explain why some tumors may have been missed on histology. A comparison of formalin fixed paraffin embedded sections to GSTP1 analysis on the same needle biopsy specimens may have resulted in more favorable results for histology. Also frozen sections make the diagnosis of high grade PIN particularly difficult. It is possible that GSTP1 analysis detected high grade PIN in some of the 9 cases missed by histology (a known histologic marker of cancer).

However all pure tumor DNA tested from these cases was strongly positive for GSTP1 and 4/4 other cases, which were subsequently reported to contain high grade PIN on formal surgical pathology review, were not found positive by GSTP1 analysis. It is therefore more likely that GSTP1 QMSP improves sensitivity by overcoming sampling error. This may be due to pure sensitivity (able to detect down to 4 cancer cells) or to the recognized field effect in many cancers, where surrounding cells to the neoplasm harbor some but not all of the genetic alterations in the primary tumor and thus do not always display neoplastic morphologic characterizations.

For the investigation and diagnosis of prostate adenocarcinoma, multiple trans-rectal needle biopsies are taken although only one needs to be found positive to establish the diagnosis. In this study, as a secondary analysis, we found that while the same number of biopsies were found positive for both tests in 37/72 cases, more biopsies from each patient with cancer were positive by GSTP1 QMSP than by histology in 31/72 cases and 4/72 cases had more biopsies positive on histology than by GSTP1 QMSP. The commonest (modal) number of positive biopsies per case was 3/6 for GSTP1 QMSP and 1/6 for histology. This supports the benefit of molecular analysis for every biopsy taken and could be especially useful for the diagnosis of very small cancers where evidence suggests that an increased number of biopsies can increase diagnostic accuracy.

In each specific case, GSTP1 levels were highest in biopsies from that case which also had the greatest extent of tumor seen on histology (as in FIG. 1). However, absolute GSTP1 values did not directly correlate with a specific amount of tumor seen on biopsy across all cases due to the wide range of GSTP1 methylation levels between different primary tumors. GSTP1 QMSP levels did not correlate with PSA values as shown previously.

At various threshold ratios from 3-10 for GSTP1 QMSP, all 11 true negative cases were negative although the confidence intervals are still wide due to the small numbers analyzed. High specificity is very important for any diagnostic test particularly when treatment options for diagnosed disease include major surgery. Even using a very conservative threshold ratio of 10 for GSTP1 QMSP, the sensitivity of diagnosis was improved substantially (11%), providing a safe way to improve diagnostic sensitivity for prostate cancer on needle biopsy.

At the very least, patients found to have negative histology but elevated GSTP1 on needle biopsy could be prioritized as high risk for early repeat biopsy to improve the chance of earliest possible diagnosis of cancer. Additional imaging techniques could also be employed to identify suspicious areas for more directed biopsies. (REF.) The addition of GSTP1 QMSP to routine (paraffin) histology is likely to improve the sensitivity of diagnostic needle biopsies by parallel amounts to that shown in this study but requires further study.

GSTP1 QMSP is a robust, reproducible and highly specific diagnostic test for prostate adenocarcinoma that could dramatically improve the sensitivity of prostate cancer diagnosis when used in combination with routine histology. Multiple pilot studies and this current prospective trial continue to support the use of this molecular approach to improve the accuracy of routine diagnostic biopsies for prostate cancer.

Example 2

Quantitative GSTP1 Hypermethylation in Bodily Fluids of Prostate Cancer Patients We investigated the potential of GSTP1 hypermethylation detection in voided urine and plasma DNA as a prostate cancer specific marker in two groups of patients, one of them harboring clinically localized prostate cancer, and a control group consisting of patients with benign prostatic hyperplasia (BPH). RTQ-MSP was used to quantify the GSTP1 methylation level. The results were compared to C-MSP. The rationale for the former approach is that RTQ-MSP allows for rapid analysis of a larger number of samples in a highly reproducible assay using small amounts of template DNA. Moreover, quantification may allow discrimination between benign and neoplastic disease, and could be useful in monitoring this disease.

Material and Methods

Patients and Sample Collection

Sixty-nine patients with clinically localized prostate adenocarcinoma, consecutively diagnosed and primarily treated with radical prostatectomy at the Portuguese Oncology Institute—Porto, were selected for this study. All cases were identified by raised serum prostate specific antigen (PSA) in routine analysis and confirmed by sextant prostate biopsy (stage T1c). Additionally, 31 patients with BPH, submitted to transurethral resection of the prostate (TURP), were included for control purposes.

All histological slides were reviewed and each tumor was staged (TNM staging system) and graded (Gleason grading system). Snap-frozen tissue stored at −80° C., or paraffin-embedded prostatic tissue was collected from each surgical specimen. Sections were cut for the identification of adenocarcinoma (radical prostatectomy specimens), and BPH (TURP tissue). For DNA extraction, these areas were microdissected from an average of fifty 12-μm thick sections for enrichment (>70%) of adenocarcinoma and hyperplastic tissue. Paraffin-embedded tissue was similarly micro-dissected, but was placed in xylene for 3 hours at 48° C. to remove the paraffin. DNA was also extracted from plasma and voided urine collected from each patient, as previously described. Briefly, DNA was digested overnight at 48° C. in 1% SDS/Proteinase K (0.5 mg/ml), extracted by phenol-chloroform, and ethanol precipitated.

Bisulfite Treatment

To perform the sodium bisulfite conversion of genomic DNA, a modification of a previously described method was used. Details of this method are given elsewhere.

Real-Time Quantitative MSP

Methylation levels of GSTP1 gene promoter and copy number of MYOD 1 gene (used as a control for the amplification quality of the template DNA) were determined by fluorescence based RTQ-MSP, as previously described.[20] Briefly, primers and probes were designed to specifically amplify either bisulfite-converted promoter DNA for the gene of interest, GSTP1. For tissue samples, the relative level of methylated GSTP1 DNA was expressed as the ratio between the values of GSTP1 versus MYOD1 obtained by the RTQ-MSP analysis, in each particular sample, and then multiplied by 1000.

All plasma and urine samples were also subjected to RTQ-MSP analysis, both for GSTP1 methylation and MYOD1 gene. The GSTP1 methylation level in bodily fluids was expressed as copies of methylated GSTP1 (genome equivalents—GE) per 50 ml for urine samples, and per 1 ml for plasma samples.[21] The specificity of the reaction for the methylated DNA was confirmed separately using a positive control (LNCaP cell line,) and a negative control (Du145 cell line). Multiple water blanks were included on each plate. The primer and probe sequences used, were described in a previous article of ours.[15]

The lowest number of genome equivalents detected by RTQ-MSP was 3.16 GE, determined by serial dilutions of the positive control (LNCaP DNA). This figure was calculated based on a conversion factor of 6.6 pg of DNA per cell.[22]

Conventional MSP

Primer sequences for either methylated or modified unmethylated GSTP1 have been described previously. C-MSP was carried out using the appropriate negative and positive controls as described above. Forty cycles of PCR were performed using an annealing temperature of 62° C. The PCR products were directly loaded onto a non-denaturing 6% polyacrylamide gel, stained with ethidium bromide, and visualized under UV illumination.

Statistical Analysis

Mann-Whitney U tests were carried out to compare the age distribution and serum PSA levels between the patients with BPH and those with adenocarcinoma. Correlations between the tumor methylation ratios and PSA level, Gleason score, and pathological stage were determined by calculating Spearman's correlation coefficient. Associations between urine or plasma GSTP1 methylation status, and pathological stage and Gleason score, were examined using the chi-square test, and Fisher's exact test. Statistical analyses were performed with Statistica for Windows, version 6.0 (StatSoft, Tulsa, Okla.), and Epi Info, version 6 (CDC, Atlanta, Ga.). Statistical significance was reached at $P<0.05$.

Results

We prospectively studied 69 patients with clinically localized prostate adenocarcinoma with a median age of 63 years (range: 52-74). As a control group, 31 patients with BPH were included (median age=64 years, range: 53-82). No statistically significant difference was found between the age distributions of these two groups (p=0.33). The median value of the preoperative serum PSA was 10.3 ng/mL (range: 1.69-48.3), and 3.43 ng/mL (range: 0.67-31), for cancer and BPH patients, respectively (p<1E-5).

Figure 3A:
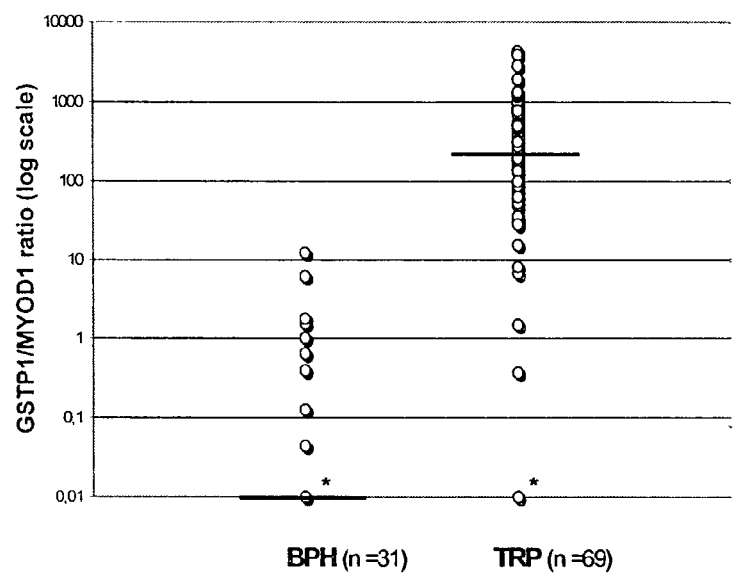
FIG. 3 shows the distribution of GSTP1 methylation levels in tissue and bodily fluids. (a) GSTP1 methylation was detected by RTQ-MSP in 29% of patients with BPH and 91.3% of patients with clinically localized prostate adenocarcinoma (TRP). Solid bars indicate the median within a group of patients. Asterisks indicate the samples with 0-values which cannot be plotted on a log scale (BPH: n=31; TRP: n=69).(b) GSTP1 methylation levels (RTQ-MSP) in positive paired urine (n=13) and plasma (n=9) samples. Solid bars indicate the median within a group of patients. Asterisks indicate the samples with 0-values which cannot be plotted on a log scale (urine: n=56; plasma: n=60).

We determined the promotor methylation status of the GSTP1 gene in the tissue samples, both for prostate cancer patients and for controls, by C-MSP and RTQ-MSP (FIG. 3a). Sixty-three of 69 (91.3%) adenocarcinomas were found to be positive for GSTP1 methylation. No correlation was found between the methylation ratio in the tumor samples and PSA levels (r=0.04, p=0.74), Gleason score (r=0.13, p=0.36), or pathological stage (r=0.23, p=0.57). In the BPH group, 9 of 31 (29%) tissue samples also showed GSTP1 hypermethylation. No discordance was found between the two MSP methods.

Figure 3B:
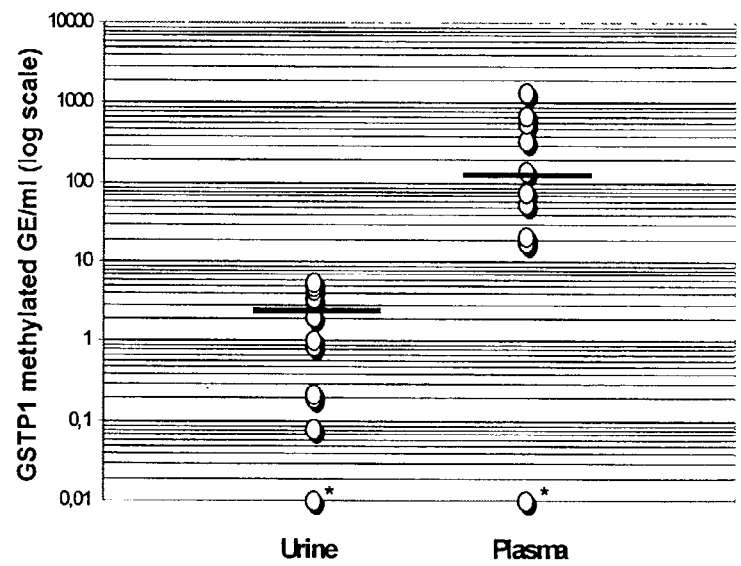

After screening for methylation changes in tissue, we analyzed the paired urine and plasma DNA samples, using both MSP methods in blinded fashion. In every case we were able to amplify DNA from all samples, i.e., tissue, urine, and plasma. GSTP1 hypermethylation was found in 13 of 69 (18.8%) urine sediments, and 9 of 69 (13.0%) plasma DNA samples from prostate cancer patients, using RTQ-MSP (FIG. 3b). The median and interquartile ranges (IQR) of GE of methylated GSTP1 were 3.039 GE/ml (IQR: 0.857-3.529), and 140.533 GE/ml (IQR: 54.6-552,267), for urine and plasma samples, respectively. C-MSP was able to detect GSTP1 methylation in 21/69 (30.4%) urines, and in 25/69 (36.2%) plasmas from the same samples.

Moreover, all cases positive for GSTP1 hypermethylation by RTQ-MSP (plasma and/or urine) where also positive by C-MSP. Importantly, there was no case in which urine sediment or plasma DNA harbored methylation when the corresponding tumor was negative. No association was found between plasma GSTP1 methylation status and pathological stage or Gleason score (p=0.84 and p=0.26, respectively). Likewise, we found no correlation between GSTP1 methylation statuses in urine samples and the pathological stage or Gleason score (p=0.09 and p=0.83, respectively).

In BPH patients, GSTP1 hypermethylation was detected in 1/31 (3.2%) urine samples, and both MSP methods were concordant (5.549 GE/ml). The matched BPH tissue did not harbor GSTP1 hypermethylation (representing a potential false positive or laboratory labeling error: see discussion below). All plasma samples from BPH patients were negative (using both methods) for GSTP1 hypermethylation.

GSTP1 promoter methylation was found in more than 90% of tumor tissue samples and to a lower degree in paired serum and urine as previously reported. These findings confirm the high frequency of this genetic alteration, and continue to support its application in DNA-based prostate cancer detection approaches. The median levels of GSTP1 hypermethylation in serum were significantly higher than urine DNA levels, by quantitative analysis (FIG. 3$b$).

This study clearly shows that higher amounts of DNA are present in plasma than in urine, especially when considering the much larger total volume that is sampled. This finding could be related to the extraction of DNA from urine sediments, i.e., predominantly from tumor cells shed in urine. Thus, it is suggested that free tumor DNA is preferentially released into the circulation rather than the prostate ductal system. These results are also consistent with the propensity of prostate cancer to disseminate early throughout the body.

Among the prostate cancer patients who had GSTP1 hypermethylation in the primary tumor, 37 (53.6%) also displayed this alteration in urine or plasma DNA using C-MSP. The number of positive cases in plasma slightly outnumbered those found in urine (36.2% vs. 30.4%). The same trend was reported in a previous study, in which 72% of patients were positive in plasma or serum, and only 36% in urine.

However, there are some major differences between Goessl et al. and our study, preventing direct comparisons between them. Goessl et al. included a large number (45%) of stage IV patients (not amenable to curable surgical resection) in which the likelihood of circulating tumor cells is rather high, perhaps resulting in a higher detection rate. Indeed, all advanced stage patients were positive for GSTP1 methylation in serum in their study. The rate of detection in urine was also superior to ours, but in their cases prostatic massage was performed previous to sample collection, increasing the shedding of prostate cells in urine.

The rate of detection in urine found in this study, reinforces the results of our previous preliminary work. Thus, several strategies can be considered to improve the detection rate of GSTP1 hypermethylation in bodily fluids. One approach would be to increased the number and/or volume of urine and plasma samples, enabling a larger sampling of tumor DNA.

Moreover, prostatic massage might increase cell shedding in urine, but this procedure could limit the acceptability of the test. Although a higher rate of GSTP1 hypermethylation was detected in ejaculates (approaching 50%), the nature of the sampling procedure, especially in older men, may preclude its widespread use. Eventually, further technical refinements of the PCR method could contribute to an increase in sensitivity, although these procedures have been substantially optimized.

The specificity of GSTP1 hypermethylation remains high since it was rarely detected in the urine and plasma DNA from patients in whom this marker was not altered in the tumor tissue. Moreover, GSTP1 methylation has not been generally detected in other genitourinary malignancies, including bladder carcinomas.

Thirty-one BPH patients, with no evidence of harboring prostate adenocarcinoma were used as controls. Although GSTP1 hypermethylation was reported to be rare in normal tissue, 9 of these patients (29%) displayed this alteration in prostatic tissue. Our findings could be explained by age-related GSTP1 hypermethylation, since recent evidence suggests that promoter methylation of certain genes in normal-appearing tissues is associated with aging. However, we saw no age-related patterns in our sample set (both BPH and cancer). Moreover, we cannot disregard the possibility that small foci of adenocarcinoma with GSTP1 hypermethylation could have been resected during the TURP procedure, along with hyperplastic glands.

In one BPH patient, GSTP1 hypermethylation was detected in urine but not in matched tissue, by both MSP methods. This result could be interpreted as a false positive, diminishing the specificity of this method. In our patients with prostate cancer no hypermethylation was detected in urine or plasma DNA of paired unmethylated tumors. Thus, it is tempting to suggest that this BPH patient could harbor occult prostate adenocarcinoma, localized in the peripheral region of the organ, not sampled by TURP. Careful follow-up may clarify this interesting observation.

In previous studies, promoter hypermethylation of several genes has been successfully used to detect tumor DNA in bodily fluids from several types of cancer, namely bronchial lavage fluid, sputum, and serum from lung cancer patients, and serum from head and neck cancer patients. In these studies, C-MSP method was found to have a high sensitivity (1:1000). However, this method does not permit quantification of the extent of gene methylation status.

In this study, a larger number of urine and plasma samples were positive for GSTP1 hypermethylation using C-MSP, comparing to RTQ-MSP (53.6% vs. 31.9%). This finding suggests that the former method is significantly more sensitive than the latter, perhaps due to the greater specificity of the internal probe designed for quantitative analysis and the high background level of fluorescence intrinsic to the RTQ-MSP analysis.

Notwithstanding, the lower limit of RTQ-MSP detection determined in the present study (3.16 GE) was more sensitive than the level reported by Lo et al. (10 GE) in myeloma. However, the amount of DNA from prostate cancer cells present in urine and plasma may be very low, impairing its detection by RTQ-MSP. Indeed, Lo and co-workers were able to detect hypermethylation in reasonable amounts of cells obtained from bone marrow aspirates of their patients.

These results suggest that RTQ-MSP could be particularly useful in the identification of neoplastic disease in cell-rich clinical material, such as needle biopsies. In this regard, RTQ-MSP has the advantage of enabling the quantification of the number of GSTP1 methylated copies, which may allow the discrimination between methylated normal tissue and carcinoma.

GSTP1 hypermethylation may be detected in urine and plasma in a large proportion of early stage prostate cancer patients harboring DNA methylation in the tissue as shown herein. Because so many patients die of prostate cancer each year, these results could have significant implications for the development of molecular approaches as adjuncts to cancer detection. Furthermore, such assays may be useful in patient monitoring and detection of minimal residual disease, once the GSTP1 methylation status of the primary tumor is established.

REFERENCES

Greenlee R T, Hill-Harmon M B, Murray T, et al: Cancer statistics, 2001. CA Cancer J Clin 51:15-36, 2001

Han M, Partin A W, Pound C R, et al: Long-term biochemical disease-free and cancer-specific survival following anatomic radical retropubic prostatectomy. The 15-year Johns Hopkins experience. Urol Clin North Am 28:555-65, 2001

Lee W H, Morton R A, Epstein J I, et al: Cytidine methylation of regulatory sequences near the pi-class glutathione S-transferase gene accompanies human prostatic carcinogenesis. Proc Natl Acad Sci U S A 91:11733-7., 1994

Lee W H, Isaacs W B, Bova G S, et al: CG island methylation changes near the GSTP1 gene in prostatic carcinoma cells detected using the polymerase chain reaction: a new prostate cancer biomarker. Cancer Epidemiol Biomarkers Prev 6:443-50., 1997

Herman J G, Graff J R, Myohanen S, et al: Methylation-specific PCR: a novel PCR assay for methylation status of CpG islands. Proc Natl Acad Sci U S A 93:9821-6, 1996

Esteller M, Corn P G, Urena J M, et al: Inactivation of glutathione S-transferase P1 gene by promoter hypermethylation in human neoplasia. Cancer Res 58:4515-8, 1998

Cairns P, Esteller M, Herman J G, et al: Molecular detection of prostate cancer in urine by GSTP1 hypermethylation. Clin Cancer Res 7:2727-30, 2001

Jeronimo C, Usadel H, Henrique R, et al: Quantitation of GSTP1 methylation in non-neoplastic prostatic tissue and organ-confined prostate adenocarcinoma. J Natl Cancer Inst 93:1747-52, 2001

Harden S V, Guo Z, Epstein J I, et al: Quantitative GSTP1 methylation clearly distinguishes between benign prostatic tissue and limited prostate adenocarcinoma. J Urol In press, 2002

Abrendt S A, Chow J T, Xu L H, et al: Molecular detection of tumor cells in bronchoalveolar lavage fluid from patients with early stage lung cancer [see comments]. J Natl Cancer Inst 91:332-9, 1999

Saiki R K, Gelfand D H, Stoffel S, et al: Primer-directed enzymatic amplification of DNA with a thermostable DNA polymerase. Science 239:487-91., 1988

Landis S H, Murray T, and Bolden S, et al: Cancer Statistics. Ca. Cancer Clin., 49:8-31, 1999.

Andriole G L, and Catalona W J: The case for aggressive diagnosis and therapy of localized prostate cancer, in: Raghavan D, Scher H I, Leibel S A, and Lange P H (Eds) *Principles and practice of genitourinary oncology*. Philadelphia. Lippincott-Raven, 1996, pp 457-464.

Isaacs W B, and Isaacs J T: Molecular genetics of prostate cancer progression, in: Raghavan D, Scher H I, Leibel S A, and Lange P H (Eds) *Principles and practice of genitourinary oncology*. Philadelphia. Lippincott-Raven, 1996, pp. 403-408.

Cairns P, Okami K, and Halachami S, et al: Frequent inactivation of PTEN/MMAC1 in primary prostate cancer. Cancer Res, 57: 4997-5000, 1997.

Lee W-H, Morton R A, and Epstein J I, et al: Cytidine methylation of regulatory sequences near the pi-class glutathione S-transferase gene accompanies human prostatic carcinogenesis. Proc Natl Acad Sci USA, 91: 11733-11737, 1994.

Lee W-H, Isaacs W B, and Bova G S, et al: CG island methylation changes near the GSTP1 gene in prostatic carcinoma cells detected using the polymerase chain reaction: a new prostate cancer biomarker. Cancer Epidemiol Biomark Prev, 6:443-450, 1997.

Esteller M, Corn P G, and Urenal J M, et al: Inactivation of Glutathione S-Transferase P1 gene by promoter hypermethylation in human neoplasia. Cancer Res, 58: 4515-4518, 1999.

Brooks J D, Weinstein M, and Lin X, et al: CG island methylation changes near the GSTP1 gene in prostatic intraepithelial neoplasia. Cancer Epidemiol Biomark Prev, 7: 531-536, 1998.

Esteller M, Sanchez-Cespedes M, and Rosell R, et al: Detection of aberrant promoter hypermethylation of tumor suppressor genes in Serum DNA from non-small cell lung cancer patients. Cancer Res, 59: 67-70, 1999.

Sanchez-Cespedes M, Esteller M, and Wu L, et al: Gene promoter hypermethylation in tumors and serum of head and neck patients. Cancer Res, 3: 1229-1235, 2000.

Cairns P, Esteller M, and Herman J G, et al: Detection of prostate cancer in urine by GSTP1 hypermethylation. Clin Cancer Res, 7: 2727-2730, 2001.

Goessl C, Krause H, and Müller M, et al: Fluorescent methylation-specific polymerase chain reaction for DNA-based detection of prostate cancer in bodily fluids. Cancer Res, 60: 5941-5945, 2000.

Heid C A, Stevens J, and Livak K J, et al: Real time quantitative PCR. Genome Res, 6: 986-994, 1996.

Lo Y M, Wong I H N, and Zhang J, et al: Quantitative analysis of aberrant p16 methylation using real-time quantitative methylation-specific polymerase chain reaction. Cancer Res, 59: 3899-3903, 1999.

Jerónimo C, Usadel H, and Henrique R, et al: Quantitation of GSTP1 methylation in non-neoplastic prostatic tissue and organ confined prostate adenocarcinoma. J Natl Cancer Inst, 93: 1747-1752, 2001.

Hermanek P, Hutter R V P, and Sobin L H, et al: Prostate, in: Hermanek P, Hutter R V P, Sobin L H, Wagner G, and Wittekind C (Eds): *Illustrated Guide to the TNM/pTNM Classification of malignant tumors*. Heidelberg, Springer-Verlag, 1997, pp: 272-280.

Gleason D F, Mellinger G T, and Veterans Administration Cooperative Urological Research group: Prediction of prognosis for prostatic adenocarcinoma by combined histologic grading and clinical staging. J Urol, 111:58-64, 1974.

Ahrendt S A, Chow J T, and Xu L-H, et al: Molecular detection of tumor cells in bronchoalveolar lavage fluid from patients with early stage lung cancer. J Natl Cancer Inst, 91: 332-339, 1999.

Olek A, Oswald J, and Walter J A: A modified and improved method of bisulfite based cytosine methylation analysis. Nucleic Acids Res, 24: 5064-5066, 1996.

Eads C A, Danenberg K D, and Kawakami K, et al: CpG island hypermethylation in human colorectal tumors is not associated with DNA methyltransferase overexpression. Cancer Res, 59: 2302-2306, 1999.

Lo Y M, Chan L Y S, and Chan A T C, et al: Quantitative and temporal correlation between circulating cell-free Epstein-Barr virus DNA and tumor recurrence in nasopharyngeal carcinoma. Cancer Res, 59: 5452-5455, 1999.

Saiki R K, Gelfand D H, and Stoffel S, et al: Primer-directed enzymatic of DNA with a thermostable DNA polymerase. Science, 239: 487-491, 1988.

Sharifi R, Shaw M, and Ray V, et al: Evaluation of cytologic techniques for diagnosis of prostate cancer. Urology, 21: 417-420, 1983.

Suh C I, Shanafelt T, and May D J, et al: Comparison of telomerase activity and GSTP1 promoter methylation in ejaculate as potential screening tests for prostate cancer. Molecular and Cellular Probes, 14: 211-217, 2000.

Ahuja N, Li Q, and Mohan A L, et al: Aging, DNA methylation in colorectal mucosa and cancer. Cancer Res, 58: 5489-5494, 1998.

Toyota M, and Issa J P: CpG island methylator phenotypes in aging and cancer. Semin Cancer Biol, 9: 349-357, 1999.

Herman J G, Graff J R, and Myohanen S, et al: Methylation-specific PCR: a novel PCR assay for methylation status of CpG islands. Proc Natl Acad Sci USA, 93: 9821-9826, 1996.

U.S. Pat. Nos. 6,265,171; 6,200,756; 6,017,704; 5,786,146; 5,552,277 (all herein incorporated by reference).

Although the invention has been described with reference to the presently preferred embodiment, it should be understood that various modifications can be made without departing from the spirit of the invention. Accordingly, the invention is limited only by the following claims.

What is claimed is:

1. A method for indicating an increased likelihood of prostate adenocarcinoma comprising:
   determining a methylation ratio of a tissue sample from a human subject with early stage cancer,
   wherein the methylation ratio is the level of methylation of a bisulfite-treated promoter region of glutathione-S-transferase (GSTP1) relative to a level of bisulfite-treated DNA copy number of a reference gene,
   wherein the early stage cancer is localized prostate cancer,
   wherein the reference gene is MYOD or ACTB,
   wherein a methylation ratio higher than the methylation ratio in tissue from a normal subject is indicative of prostate adenocarcinoma in the subject, and
   wherein a methylation ratio times 1000 of greater than about 3 is indicative of prostate adenocarcinoma in the subject.

2. The method of claim 1, wherein the sample is biological fluid.

3. The method of claim 1, wherein the sample is serum, plasma, ejaculate, or urine.

4. The method of claim 1, wherein the sample is prostate tissue sample.

5. The method of claim 1, wherein the level of methylation is determined by using real-time polymerase chain reaction (PCR).

6. The method of claim 1, wherein the level of methylation is determined by using real-time polymerase chain reaction (PCR), wherein at least one primer used in the PCR is capable of distinguishing between unmethylated and methylated nucleic acid.

7. The method of claim 1, wherein the level of methylation is determined by using real-time polymerase chain reaction (PCR), wherein both primers used in the PCR are capable of distinguishing between unmethylated and methylated nucleic acid.

8. The method of claim 1, wherein the level of methylation is determined by using real-time polymerase chain reaction (PCR), wherein a probe used in the PCR is capable of distinguishing between unmethylated and methylated nucleic acid.

9. The method of claim 1, wherein the level of methylation is determined by using real-time polymerase chain reaction (PCR), wherein both primers and a probe used in the PCR are capable of distinguishing between unmethylated and methylated nucleic acid.

10. The method of claim 1, wherein the reference gene is MYOD or ACTB.

11. The method of claim 1, wherein the level of the region in the reference gene is determined by using real-time polymerase chain reaction (PCR).

12. The method of claim 1, wherein the level of the region in the reference gene is determined by using real-time polymerase chain reaction (PCR), wherein the region contains a first and second primer binding site and a probe binding site and wherein the first and second primer binding site and the probe binding site are devoid of CpG dinucleotides.

13. The method of claim 1, wherein the region in the reference gene is devoid of CpG dinucleotides.

14. The method of claim 1, wherein a methylation ratio times 1000 of greater than about 5 is indicative of prostate adenocarcinoma in the subject.

15. The method of claim 1, wherein a methylation ratio times 1000 of greater than about 10 is indicative of prostate adenocarcinoma in the subject.

16. The method of claim 1 further comprising conducting a histological analysis of the sample, wherein the sample is prostate tissue sample.

17. The method of claim 1 further comprising conducting a histological analysis of the sample, wherein the sample is prostate tissue sample and wherein a negative diagnosis as indicated by the histological analysis and a methylation ratio greater than 5 is indicative of prostate adenocarcinoma in the subject.

18. The method of claim 1 further comprising conducting a histological analysis of the sample, wherein the sample is prostate tissue sample and wherein a negative diagnosis as indicated by the histological analysis and a methylation ratio greater than 10 is indicative of prostate adenocarcinoma in the subject.

19. The method of claim 1 wherein the sample is prostate tissue sample and the subject has a negative diagnosis of prostate adenocarcinoma as indicated by a histological analysis of the sample.

20. The method of claim 1, wherein the sample is prostate tissue sample and the subject has a negative diagnosis of prostate adenocarcinoma as indicated by a histological analysis of the sample and a methylation ratio greater than 5 is indicative of prostate adenocarcinoma in the subject.

21. The method of claim 1, wherein the sample is prostate tissue sample and the subject has a negative diagnosis of prostate neoplasia or prostate adenocarcinoma as indicated by a histological analysis of the sample and a methylation ratio greater than 10 is indicative of prostate adenocarcinoma in the subject.

22. The method of claim 1, further comprising measuring PSA level of the subject.

23. The method of claim 1, wherein the subject has a normal PSA level.

24. The method of claim 1, wherein the subject has a PSA level higher than a normal PSA level.

25. A method for indicating an increased likelihood of prostate adenocarcinoma comprising:

amplifying a promoter region of glutathione-S-transferase (GSTP1) in a biological sample from a subject with early stage cancer by means of oligonucleotide primers in the presence of at least one specific oligonucleotide probe, wherein the early stage cancer is localized prostate cancer, wherein the promoter region is modified by an agent that modifies unmethylated cytosine to produce a converted nucleic acid, wherein the agent is sodium-bisulfite and wherein at least one oligonucleotide primer or specific oligonucleotide probe is capable of distinguishing between unmethylated and methylated nucleic acid, determining the methylation level of the promoter region by determining the amplification level of the promoter region based on amplification-mediated displacement of the specific oligonucleotide probe, wherein a methylation level higher than the methylation level in a normal subject is indicative of prostate adenocarcinoma in the subject.

26. The method of claim 25, wherein the biological sample is prostate tissue sample, serum, plasma, ejaculate, or urine.

27. The method of claim 25, wherein the amplifying step is a polymerase chain reaction (PCR).

28. The method of claim 25, wherein the agent is bisulfite.

29. The method of claim 25, wherein at least two oligonucleotide primers are capable of distinguishing between methylated and unmethylated nucleic acid.

30. The method of claim 25, wherein at least one specific oligonucleotide probe is capable of distinguishing between methylated and unmethylated nucleic acid.

31. The method of claim 25, wherein the specific oligonucleotide probe further comprises at least one fluorescence label moiety.

32. The method of claim 1 or 25, wherein the clinically localized cancer is surgically resectable.

* * * * *